(12) United States Patent
Chung

(10) Patent No.: US 10,881,543 B2
(45) Date of Patent: Jan. 5, 2021

(54) LUMBAR SUPPORT ASSISTIVE DEVICE

(71) Applicant: Kun-Yen Chung, Tainan (TW)

(72) Inventor: Kun-Yen Chung, Tainan (TW)

( * ) Notice: Subject to any disclaimer, the term of this patent is extended or adjusted under 35 U.S.C. 154(b) by 249 days.

(21) Appl. No.: 16/120,453

(22) Filed: Sep. 4, 2018

(65) Prior Publication Data
US 2019/0290467 A1 Sep. 26, 2019

(30) Foreign Application Priority Data

Mar. 22, 2018 (TW) .............................. 107109811 A

(51) Int. Cl.
*A61F 5/02* (2006.01)
*A47C 16/00* (2006.01)

(52) U.S. Cl.
CPC ............ *A61F 5/028* (2013.01); *A47C 16/005* (2013.01); *A61F 5/024* (2013.01)

(58) Field of Classification Search
CPC ... A61H 2205/081; A61H 39/04; A61F 5/024; A61F 5/028; A47C 16/005
See application file for complete search history.

(56) References Cited

U.S. PATENT DOCUMENTS

| | | | | |
|---|---|---|---|---|
| 4,421,110 A * | 12/1983 | DeLisle | ................. | A61H 7/001 601/134 |
| 5,127,897 A * | 7/1992 | Roller | ..................... | A61F 5/024 128/107.1 |
| 5,290,307 A * | 3/1994 | Choy | ..................... | A61H 39/04 128/101.1 |
| 5,571,076 A * | 11/1996 | Cooper | .............. | A41D 13/0531 2/44 |
| 6,036,719 A * | 3/2000 | Meilus | ................... | A61H 1/008 601/134 |
| 8,888,808 B1 * | 11/2014 | Park | ...................... | A61M 21/02 606/204 |
| 2004/0147959 A1 * | 7/2004 | Shin | ....................... | A61H 39/04 606/240 |
| 2006/0241538 A1 * | 10/2006 | Chen | ..................... | A61H 7/001 601/134 |
| 2009/0259151 A1 * | 10/2009 | McDonnell | ..................... | 601/56 |
| 2010/0145244 A1 * | 6/2010 | Schwartz | ............... | A61H 39/04 601/134 |
| 2012/0179201 A1 * | 7/2012 | Segur | ..................... | A61H 1/008 606/237 |
| 2013/0317539 A1 * | 11/2013 | Armm | .................... | A61H 39/04 606/204 |

* cited by examiner

Primary Examiner — Kari K Rodriquez
(74) Attorney, Agent, or Firm — Leong C. Lei

(57) ABSTRACT

The lumbar support assistive device includes a plastic rigid main member having a half-fusiform whose front side curves in accordance with human spine. A trough is provided along the front side extended in an axial direction to a bottom side of the main member. A number of forward bulging semi-ellipsoidal elements are arranged at intervals in two columns along lateral sides of the trough. The semi-ellipsoidal elements closer to a bottom of the main member are wider and higher; and the semi-ellipsoidal elements closer to a top of the main member are narrower and lower, and they are closer to the semi-ellipsoidal elements in the other column. These semi-ellipsoidal elements provide massaging effect and support to corresponding intervertebral discs of the spine. The semi-ellipsoidal elements also raise the lumbar support assistive device to provide enhanced ventilation so that wearing the lumbar support assistive device would not feel sultry.

9 Claims, 4 Drawing Sheets

LUMBAR SUPPORT ASSISTIVE DEVICE

BACKGROUND OF THE INVENTION

(a) Technical Field of the Invention

The present invention is generally related to assistive devices, and more particular to a lumbar support assistive device.

(b) Description of the Prior Art

Various assistive devices have been provided to ease waist pain resulted from people's long standing or sitting postures and from repetitive lifting heavy objects in their daily lives or work. High pressure is accumulated around their intervertebral discs, causing fatigue, deformation, and discomfort. These assistive devices generally involve a wide belt such as the one taught by R.O.C. Taiwan Patent No. M541288 where support plates are embedded in the wide belt. As the belt is fastened to a user's waist, it provides support the user's spine when the user stands or sits and prevents muscle or nerve around the waist or spine from overstressing and damaging. However, for this kind of belt-based assistive devices, they provide little support if the belt is too lose. On the other hand, discomfort is inevitable if the belt is too tight. Especially for those wide belts wrapping around users' waists, the users would often feel sultry after a period of usage. Therefore, there is a need for an improved assistive device that may provide adequate spine support and protection when people stand, sit, or move objects for a long period of time, but is also convenient and comfortable to use.

SUMMARY OF THE INVENTION

The present invention teaches a novel lumbar support assistive device that includes a plastic rigid main member having a half-fusiform whose front side curves in accordance with human spine. A trough is provided along the front side extended in an axial direction to a bottom side of the main member. A number of forward bulging semi-ellipsoidal elements are arranged at intervals in two columns along lateral sides of the trough. The semi-ellipsoidal elements closer to a bottom of the main member are wider and higher; and the semi-ellipsoidal elements closer to a top of the main member are narrower and lower, and they are closer to the semi-ellipsoidal elements in the other column. These semi-ellipsoidal elements provide massaging effect and support to corresponding intervertebral discs of the spine. The semi-ellipsoidal elements also raise the lumbar support assistive device to provide enhanced ventilation so that wearing the lumbar support assistive device would not feel sultry.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
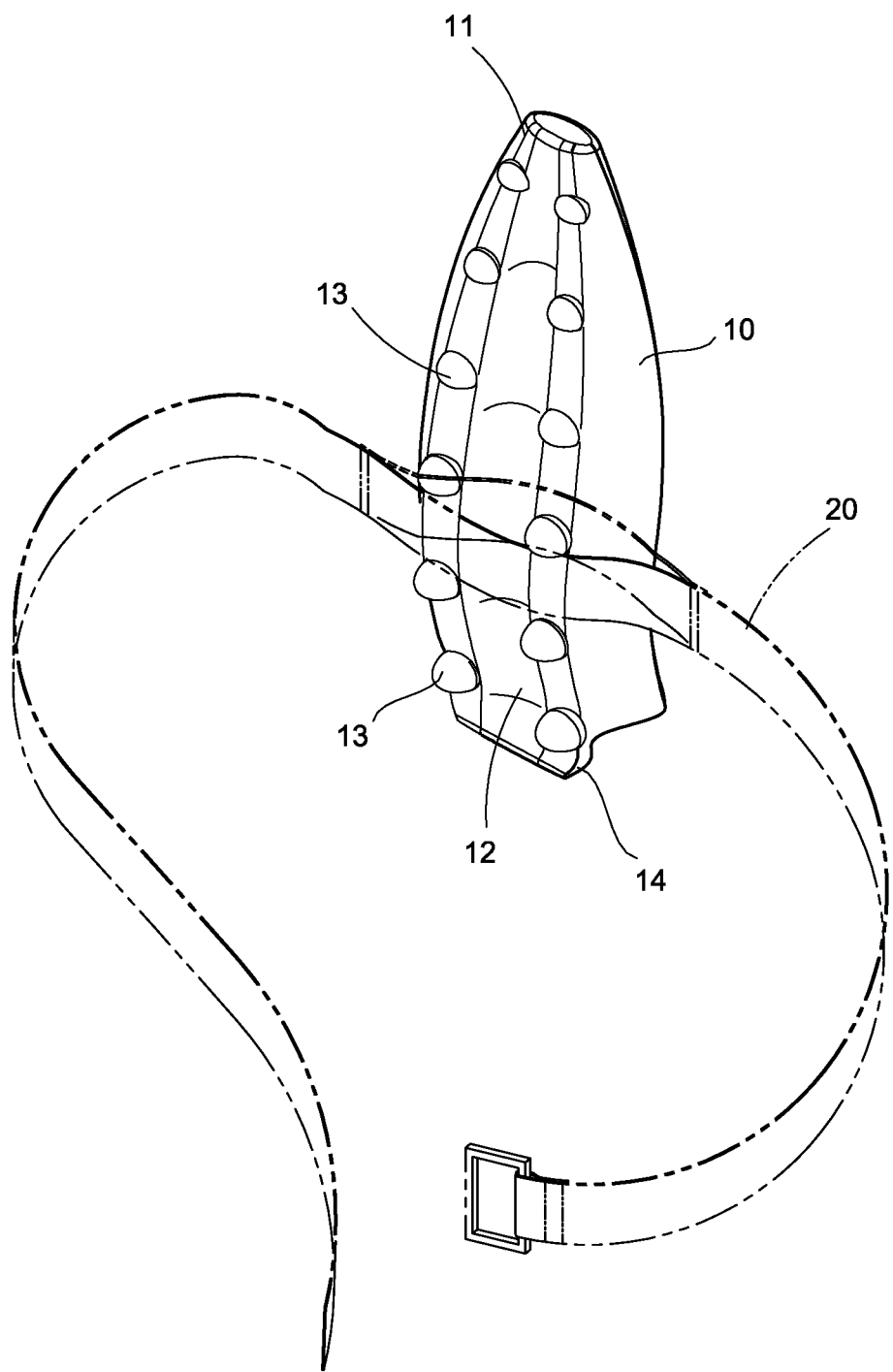
FIG. 1 is a perspective diagram showing a lumbar support assistive device according to an embodiment of the present invention.
Figure 2:
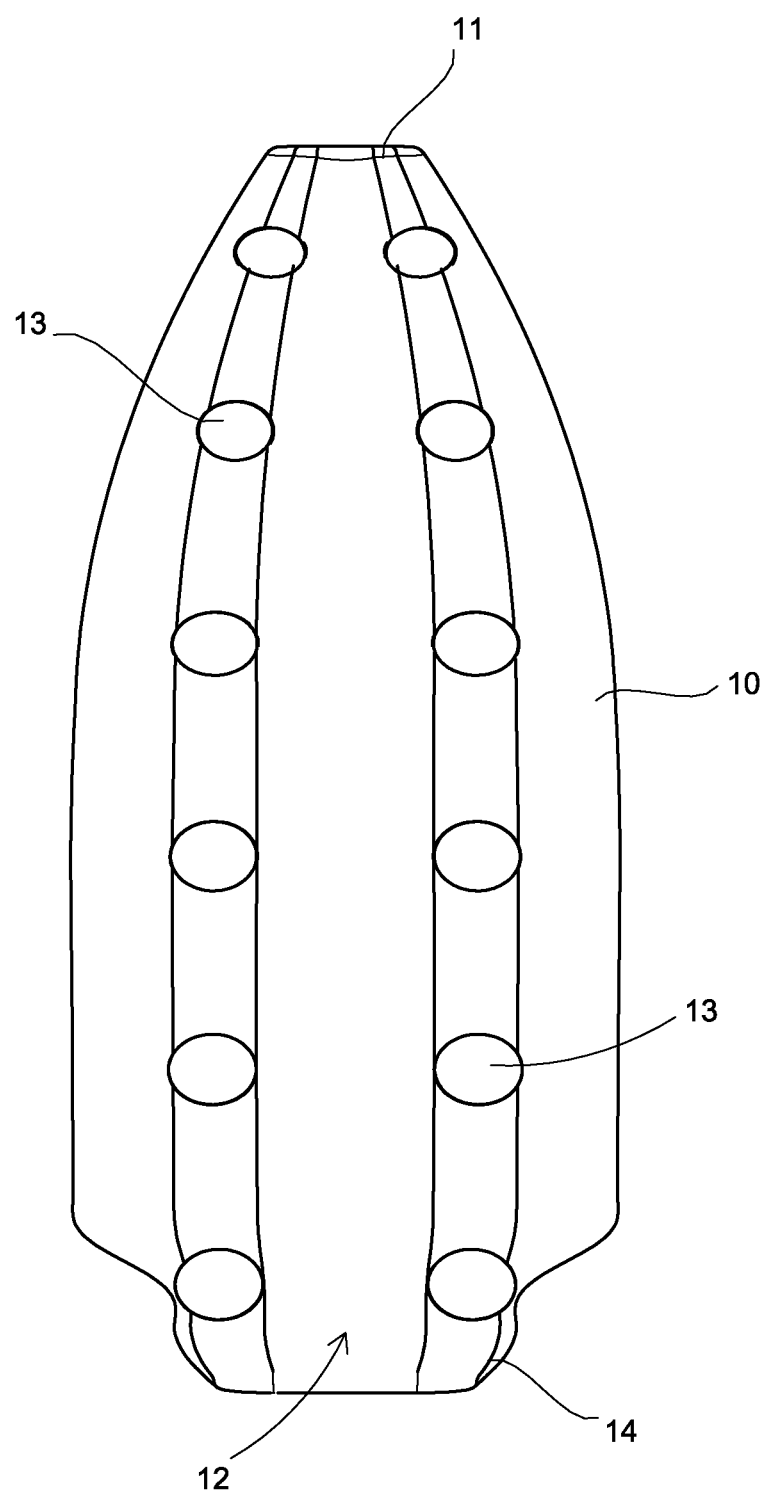
FIG. 2 is a front-view diagram showing the lumbar support assistive device of FIG. 1.
Figure 3:
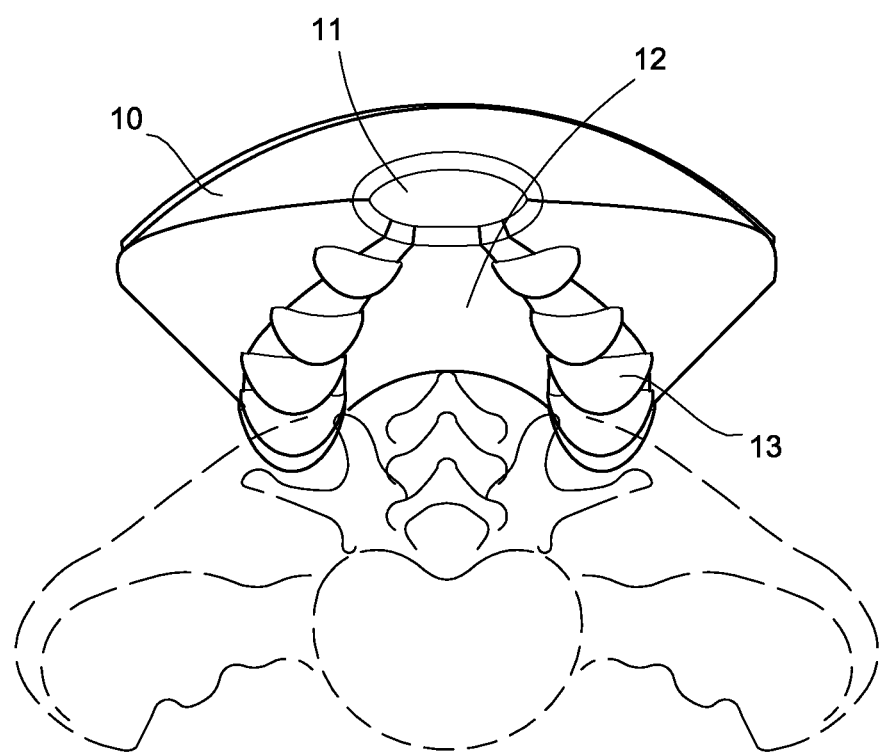
FIG. 3 is a top-view diagram showing the lumbar support assistive device of FIG. 1.
Figure 4:
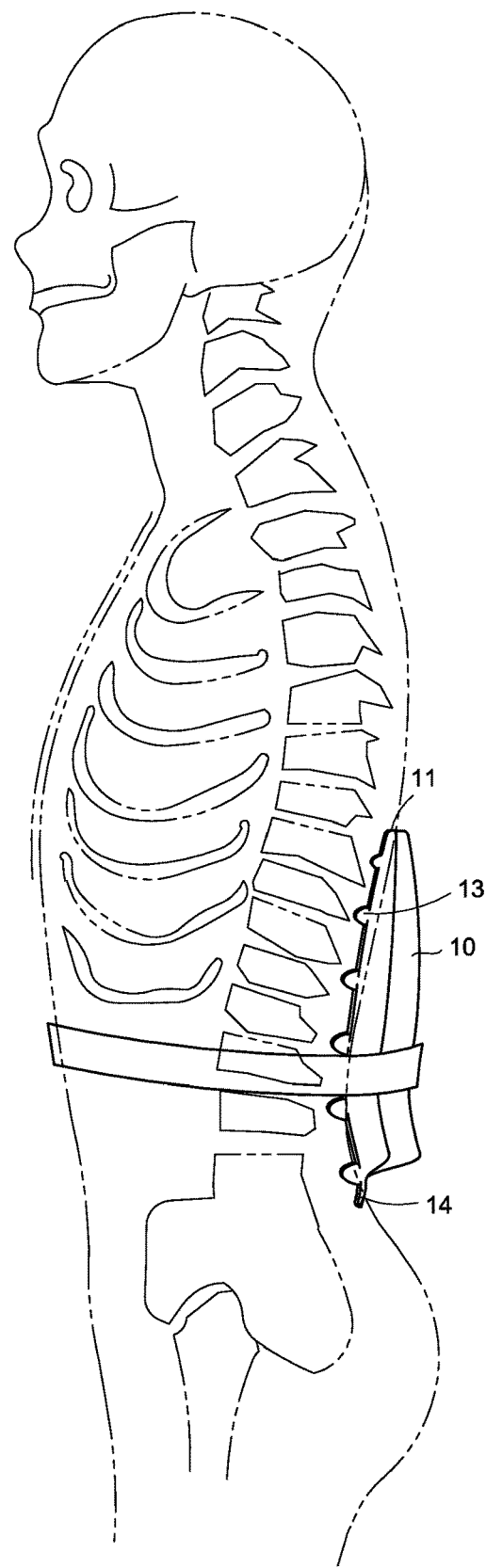
FIG. 4 is a schematic side-view diagram showing the lumbar support assistive device of FIG. 1 worn by a user.

The present invention teaches a lumbar support assistive device, as shown in FIGS. 1 to 4, including a plastic-molded, half-fusiform main member 10 shaped similar to cuttlebone. A front side of the main member 10 curves in accordance with human spine. Depending on different user postures, the main member 10 has a width 7~11 cm and a length 185~210 mm. For a user of height 170 cm, the main member 10 has a width 9 cm and a length 200 mm for better comfort and wearing reliability. The main member 10 is made of relatively hard rubber, plastic, or Acrylonitrile Butadiene Styrene (ABS) material whose Shore hardness is between 60 and 80 degrees. To achieve a greater comfort, a plastic layer 11 made of environmentally friendly silicone or a flexible environmentally friendly material of thickness 2~5 mm may be directly attached to the front side of or sleeved over the main member 10. A belt 20 is provided to run across a middle section of the main member 10 for conveniently wearing and positioning the main member 10. A trough 12 is provided along the front side of the main member 10 extended in the axial direction to a bottom side of the main member 10. Two columns of forward bulging semi-ellipsoidal elements 13 are provided along the lateral sides of the trough 12. The semi-ellipsoidal elements 13 are disposed at 3-5 cm intervals within each column. The semi-ellipsoidal elements 13 have bulging heights 14~8.5 mm, and widths 13.5~9 mm. The semi-ellipsoidal elements 13 closer to the bottom of the main member 10 are wider and higher. The bottommost semi-ellipsoidal elements 13 have the greatest bulging heights. The semi-ellipsoidal elements 13 closer to the top of the main member 10 are narrower and lower, and they are closer to the semi-ellipsoidal elements 13 in the other column. These semi-ellipsoidal elements 13 provide massaging effect and support to the corresponding intervertebral discs of the spine. The semi-ellipsoidal elements 13 also raise the lumbar support assistive device to provide enhanced ventilation so that wearing the lumbar support assistive device would not feel sultry. On the other hand, the indented trough 12 provides leeway to the spine so that the user would not feel his/her spine being pressed and uncomfortable. Furthermore, the bulging semi-ellipsoidal elements 13 provide additional support when the user sits down, stand up, or lifts heavy objects and as such prevents the user from hurting his/her spine. A tail piece 14 is provided to the bottom side of the main member 10 for tugging into the user's clothes. The tail piece 14 also provides a reliable positioning to the main member 10 so that the main member 10 does not slide. The tail piece 14 is preferably made of a flexible material so that it does not cause discomfort when the assistive device is in use. Together with the simple and elastic belt 20, the assistive device may be reliably positioned and worn. The assistive device as such may naturally become an integral part of the user's body while the semi-ellipsoidal elements 13 provide support and massaging.

The gist of the present invention is as follows. The main member 10 is positioned around a user's lumbar for superior support. The plastic layer 11 provides a comfort contact surface. The trough 12 allows leeway to the spine to avoid the discomfort of pressing and contacting the spine. The semi-ellipsoidal elements 13 to the sides of the trough 12 reliably press the two sides of the intervertebral discs and raise the main member from the user's back for enhanced ventilation. The user would not feel sultry even after long period of usage. Especially, the decreasing heights of the semi-ellipsoidal elements 13 as they are positioned higher provide complete support to the spine and enhanced massaging as the user moves. The tail piece 14 provides addition positioning to the main member as it may be tugged into waist belt or clothes. The belt 20 further provides reliable fastening of the main member 10 to the user's waist. The curved front side and rigid material of the main member 10 jointly provide comfort and support.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. A lumbar support assistive device, comprising:
a plastic rigid main member having a half-fusiform whose front side curves in accordance with human spine;
a trough along the front side extended in an axial direction to a bottom side of the main member;
a plurality of forward bulging semi-ellipsoidal elements arranged at intervals in two columns along lateral sides of the trough; and
a tail piece extended from a bottom side of the main member for tugging inside clothes and positioning the main member;
wherein
the semi-ellipsoidal elements have decreasing bulging heights and widths as they are positioned higher on the main member so that the bottommost semi-ellipsoidal elements have the greatest bulging heights and widths and the topmost semi-ellipsoidal elements have the smallest bulging heights and widths; and
the semi-ellipsoidal elements have decreasing distances from the semi-ellipsoidal elements in the other column as they are positioned higher on the main member so that the bottommost semi-ellipsoidal elements in the two columns have the greatest distance and the topmost semi-ellipsoidal elements in the two columns have the smallest distance.

2. The lumbar support assistive device according to claim 1, wherein the main member has a length 185-210 mm and a width 7-11 cm.

3. The lumbar support assistive device according to claim 1, wherein the semi-ellipsoidal elements are disposed at 3-5 cm intervals within each column.

4. The lumbar support assistive device according to claim 1, wherein the semi-ellipsoidal elements have bulging heights 14-8.5 mm, and widths 13.5-9 mm.

5. The lumbar support assistive device according to claim 1, wherein the main member is made of a hard rubber, plastic, or Acrylonitrile Butadiene Styrene (ABS) material.

6. The lumbar support assistive device according to claim 5, wherein the material has a Shore hardness between 60 and 80 degrees.

7. The lumbar support assistive device according to claim 1, further comprising a plastic layer of a thickness 2-5 mm on the front side of the main member.

8. The lumbar support assistive device according to claim 7, wherein the plastic layer is made of environmentally friendly silicone or a flexible environmentally friendly material.

9. The lumbar support assistive device according to claim 1, wherein the tail piece is made of a flexible material.

* * * * *